United States Patent
Yehia et al.

(10) Patent No.: US 10,500,244 B1
(45) Date of Patent: Dec. 10, 2019

(54) **SYNTHESIS OF BLACK EGGPLANT (*SOLANUM MELONGENA*) SKIN ANTIOXIDANT NANOPARTICLES**

(71) Applicant: KING SAUD UNIVERSITY, Riyadh (SA)

(72) Inventors: Hany Mohamed Yehia, Helwan (EG); Mohamed Fekry Serag El-Din, Riyadh (SA); Hatem Salama Mohamed Ali, Cairo (EG); Mohamed Saleh Alamri, Riyadh (SA); Wafa Abdullah Al-Megrin, Riyadh (SA); Manal Fawzy Elkhadragy, Hewan (EG); Manal Ahmed Gasmelseed Awad, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/408,992

(22) Filed: May 10, 2019

(51) Int. Cl.
*A61K 36/81* (2006.01)
*A61K 9/16* (2006.01)

(52) U.S. Cl.
CPC .............. *A61K 36/81* (2013.01); *A61K 9/16* (2013.01); *A61K 9/1682* (2013.01); *A61K 2236/33* (2013.01); *A61K 2236/39* (2013.01); *A61K 2236/51* (2013.01)

(58) Field of Classification Search
CPC .................................................. A61K 36/81
See application file for complete search history.

(56) References Cited

U.S. PATENT DOCUMENTS

2004/0249138 A1   12/2004   Lawson

FOREIGN PATENT DOCUMENTS

| CN | 103146389 A | 6/2013 |
| CN | 107941764 A | 4/2018 |
| KR | 101434219 B1 | 8/2014 |
| KR | 20180053946 A | 5/2018 |

OTHER PUBLICATIONS

Azevedo et al., "Differential response related to genotoxicity between eggplant (*Solanum melanogena*) skin aqueous extract and its main purified anthocyanin (delphinidin) in vivo," Food and Chemical Toxicology 45(5):852-858, 2007.*
Azevedo, L., et al., "Differential response related to genotoxicity between eggplant (*Solanum melanogena*) skin aqueous extract and its main purified anthocyanin (delphinidin) in vivo," Food and Chemical Toxicology, 45(5): 852-858, 2007.
Cao, G., et al., "Antioxidant Capacity of Tea and Common Vegetables," J. of Ag. and Food Chem. 44(11): 3426-3431, 1996.

(Continued)

*Primary Examiner* — Rosanne Kosson
(74) *Attorney, Agent, or Firm* — Richard C. Litman; Nath, Goldberg & Meyer

(57) ABSTRACT

The black eggplant skin antioxidant nanoparticles may be manufactured by extracting black eggplant skins in a solvent, spraying the black eggplant skin extracts into boiling water under ultrasonic conditions to produce a first mixture, sonicating the mixture, stirring the mixture, and drying the mixture to obtain black eggplant skin antioxidant nanoparticles. In an embodiment, the black eggplant skin may be skin of *Solanum melongena*. In an embodiment, the black eggplant skin nanoparticles may have improved antibacterial or antioxidant properties.

10 Claims, 3 Drawing Sheets

(56) References Cited

OTHER PUBLICATIONS

Hanson, P. M., et al., "Diversity in eggplant (*Solanum melongena*) for superoxide scavenging activity, total phenolics, and ascorbic acid," J. of Food Composition and Analysis 19(6-7): 594-600, 2006.
Huang, M.-T., and Ferraro, T., "Phenolic Compounds in Food and Cancer Prevention," Phenolic Compounds in Foods and Their Effects on Health II, (2): 8-34, 1992.
Hang, L., et al., "Fruit and Vegetable Intake and Risk of Major Chronic Disease," J. of the National Cancer Institute 97(8): 607-609, 2004.
Noda, Y., et al., "Antioxidant activity of nasunin, an anthocyanin in eggplant peels," Toxicology 148(2-3): 119-123, 2000.

* cited by examiner

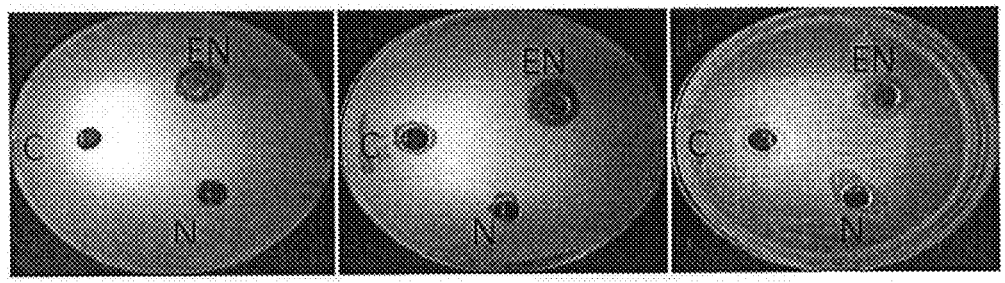
1- *Bacillus subtilis*  
FIG. 3A
2- *Micrococcus luteus*  
FIG. 3B
3- *Enterococcus faecalis*  
FIG. 3C
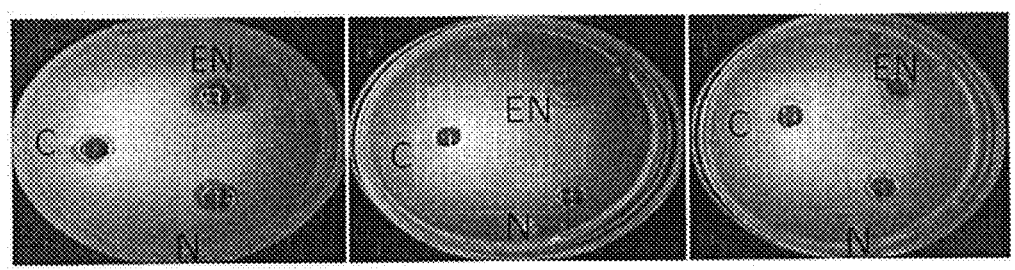
4- *Listeria innocua*  
FIG. 3D
5- *Listeria monocytogenes*  
FIG. 3E
6- *Staphylococcus aureus*  
FIG. 3F
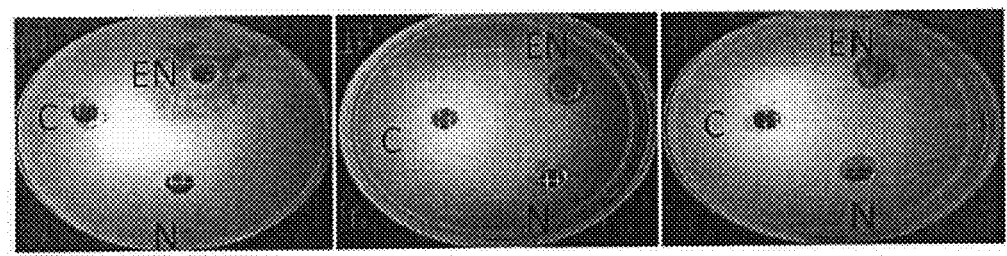
7- *Serratia marcescens*  
FIG. 3G
8- *Pseudomonas aeruginosa*  
FIG. 3H
9- *Salmonella typhimurium*  
FIG. 3I

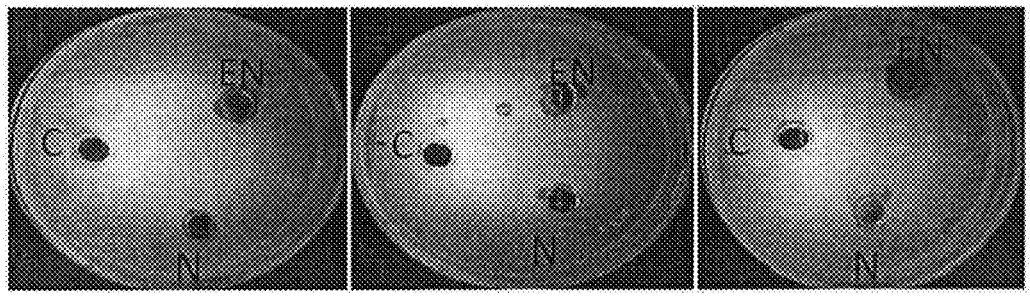
10- *Klebsiella pneumoniae*  FIG. 3J
11- *Escherichia coli*  FIG. 3K
12- *Yersina enterocolitica*  FIG. 3L
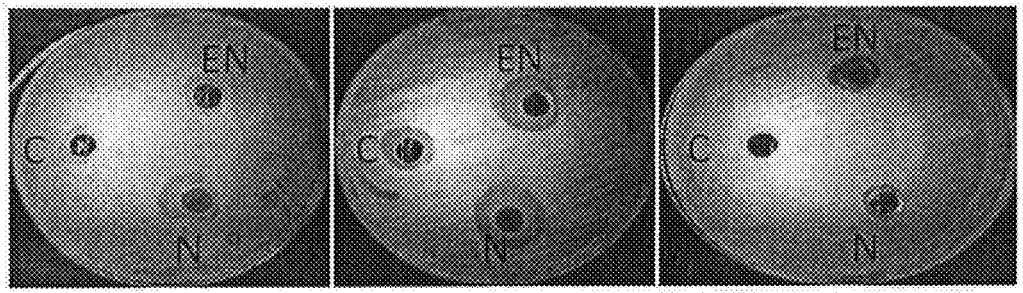
13- *Rhodotorula glutinis*  FIG. 3M
14- *Saccharomyces cerevisiae*  FIG. 3N
15- *Bacillus subtilis subsp. spizizenii*  FIG. 3O

SYNTHESIS OF BLACK EGGPLANT (*SOLANUM MELONGENA*) SKIN ANTIOXIDANT NANOPARTICLES

BACKGROUND

1. Field

The disclosure of the present patent application relates to nanotechnology, and particularly to synthesis of black eggplant (*Solanum melongena*) skin antioxidant nanoparticles.

2. Description of the Related Art

In materials science, nanomaterials have demonstrated unique size and morphology based characteristics. Nanotechnology is an emerging field demonstrating significant potential for the development of new medicines. The most common methods of producing nanoparticles are chemical or mechanical, including ball milling, thermal quenching, precipitation techniques, and vapor deposition. However, these methods are often costly, and may result in toxic byproducts.

Biological approaches for synthesizing nanoparticles can avoid many of the disadvantages associated with the chemical or mechanical synthesis methods.

In recent years, vegetables have been considered as a potential source of antioxidants. Diets rich in antioxidant containing vegetables have been linked to reduced risk of coronary heart disease, neurodegenerative disease, and certain forms of cancer. However, antioxidant rich vegetables are not readily available throughout the year in many locations. Further, the antioxidant activities of different natural sources may vary significantly, depending upon growth conditions and methods of preparation.

Thus, black eggplant (*Solanum melongena*) skin antioxidant nanoparticles solving the aforementioned problems are desired.

SUMMARY

Black eggplant skin nanoparticles may be manufactured by extracting black eggplant skins in a solvent, spraying the black eggplant skin extracts into boiling water under ultrasonic conditions to produce a first mixture, stirring the mixture, and drying the mixture to obtain black eggplant skin nanoparticles. In an embodiment, the black eggplant skin may be skin of *Solanum melongena*. In an embodiment, the solvent may be methanol.

An embodiment of the present subject matter is directed to a pharmaceutical composition comprising the black eggplant skin nanoparticles and a pharmaceutically acceptable carrier.

An embodiment of the present subject matter is directed to a method of making a pharmaceutical composition including mixing the black eggplant skin nanoparticles with a pharmaceutically acceptable carrier.

These and other features of the present disclosure will become readily apparent upon further review of the following specification and drawings.

BRIEF DESCRIPTION OF THE DRAWINGS

FIG. 3A depicts the zone of inhibition of black eggplant skin nanoparticles/extract on *Bacillus subtilis*.

FIG. 3B depicts the zone of inhibition of black eggplant skin nanoparticles/extract on *Micrococcus luteus*.

FIG. 3C depicts the zone of inhibition of black eggplant skin nanoparticles/extract on *Enterococcus faecalis*.

FIG. 3D depicts the zone of inhibition of black eggplant skin nanoparticles/extract on *Listeria innocua*.

FIG. 3E depicts the zone of inhibition of black eggplant skin nanoparticles/extract on *Listeria monocytogenes*.

FIG. 3F depicts the zone of inhibition of black eggplant skin nanoparticles/extract on *Staphylococcus aureus*.

FIG. 3G depicts the zone of inhibition of black eggplant skin nanoparticles/extract on *Serratia marcescens*.

FIG. 3H depicts the zone of inhibition of black eggplant skin nanoparticles/extract on *Pseudomonas aeruginosa*.

FIG. 3I depicts the zone of inhibition of black eggplant skin nanoparticles/extract on *Salmonella typhimurium*.

FIG. 3J depicts the zone of inhibition of black eggplant skin nanoparticles/extract on *Klebsiella pneumoniae*.

FIG. 3K depicts the zone of inhibition of black eggplant skin nanoparticles/extract on *Escherichia coli*.

FIG. 3L depicts the zone of inhibition of black eggplant skin nanoparticles/extract on *Yersinia enterocolitica*.

FIG. 3M depicts the zone of inhibition of black eggplant skin nanoparticles/extract on *Rhodolorula glulinis*.

FIG. 3N depicts the zone of inhibition of black eggplant skin nanoparticles/extract on *Saccharomyces cerevisiae*.

FIG. 3O depicts the zone of inhibition of black eggplant skin nanoparticles/extract on *Bacillus subtilis* subsp. *spizizenii*.

Similar reference characters denote corresponding features consistently throughout the attached drawings.

DETAILED DESCRIPTION OF THE PREFERRED EMBODIMENTS

Figure 1:
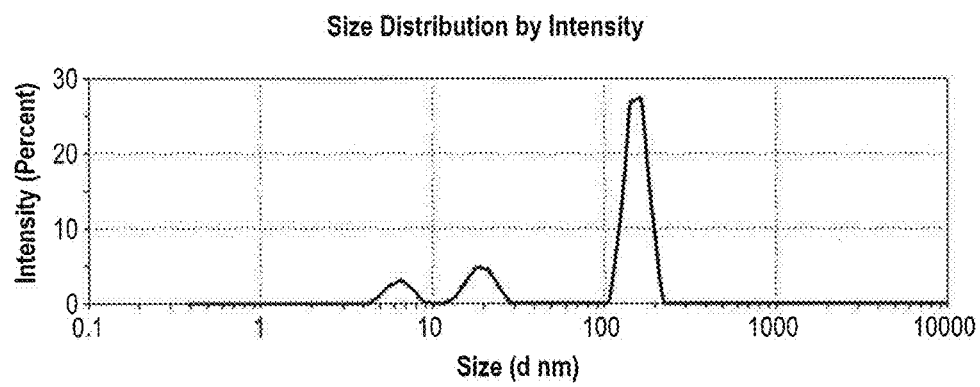
FIG. 1 depicts a zetasizer spectrum of the black eggplant skin nanoparticle size distribution.

The black eggplant skin nanoparticles may be manufactured by extracting black eggplant skins in a solvent, spraying the black eggplant skin extracts into boiling water under ultrasonic conditions to produce a first mixture, sonicating the mixture, stirring the mixture, and drying the mixture to obtain black eggplant skin nanoparticles. In an embodiment, the black eggplant skin may be skin of *Solanum melongena*. In an embodiment, the solvent may be methanol.

As used herein, the term "about," when used to modify a numerical value, means within ten percent of that numerical value.

In an embodiment, about 500 mg of black eggplant skins may be extracted in about 20 ml of methanol under constant stirring to produce a black eggplant skin extract.

In an embodiment, the black eggplant skin extract (e.g., about 40 ml) may be sprayed into about 40 ml boiling water, dropwise, with a flow rate of about 0.2 ml/min, over about 5 minutes in ultrasonic conditions to provide a mixture. In this embodiment, the ultrasonic conditions may be 750 W of ultrasonic power at a frequency of 20 kHz.

In an embodiment, the mixture may be sonicated for a further 10 minutes.

In an embodiment, the stirring may be at 200-800 rpm at room temperature, for about 20 minutes.

An embodiment of the present subject matter is directed to a pharmaceutical composition comprising the black eggplant skin nanoparticles and a pharmaceutically acceptable carrier.

An embodiment of the present subject matter is directed to a method of making a pharmaceutical composition including mixing the black eggplant skin nanoparticles with a pharmaceutically acceptable carrier. For example, the method of making a pharmaceutical composition can include mixing the black eggplant skin nanoparticles under sterile conditions with a pharmaceutically acceptable carrier with preservatives, buffers, and/or propellants to create the pharmaceutical composition.

An embodiment of the present subject matter is directed to a pharmaceutical composition including the black eggplant skin nanoparticles. To prepare the pharmaceutical composition, the black eggplant skin nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

The following examples illustrate the present teachings.

Example 1

Synthesis and Characterization of Black Eggplant Skin Nanoparticles and Black Eggplant Skin Extracts Black eggplant skin extracts were synthesized as follows. Black eggplants (*Solanum melongena*) were purchased in Riyadh, Saudi Arabia. The black eggplant skins were separated from the fruits, cut into small pieces, then dried in an oven at 60° C. for 24 hours. The dried black eggplant skins were soaked in methanol (100 mg/ml) overnight in a shaker, producing black eggplant skin extract mixtures. The resulting black eggplant skin extract mixtures were centrifuged at 5,000 rpm for 5 minutes, and the supernatants or black eggplant skin extracts, were filtered using Whatman® No. 41 filter paper and collected for testing.

Black eggplant skin nanoparticles were synthesized as follows. Black eggplant skins (about 500 mg) were extracted in about 20 ml of methanol under constant stirring to produce a black eggplant skin extract. The black eggplant skin extract was sprayed into boiling water (40 ml) dropwise, with a flow rate of 0.2 ml/min, over 5 minutes, under ultrasonic conditions (ultrasonic power 750 W, frequency 20 kHz) to produce a mixture. The mixture was sonicated for a further 10 min, stirred at 200-800 rpm at room temperature for 20 min, and dried to obtain black eggplant skin nanoparticles.

The average size of the black eggplant skin nanoparticles was measured by zetasizer. As illustrated in FIG. 1, the black eggplant skin nanoparticles have an average particle size (diameter) that varies from about 1 nm to about 200 nm.

Figures 2A, 2B:
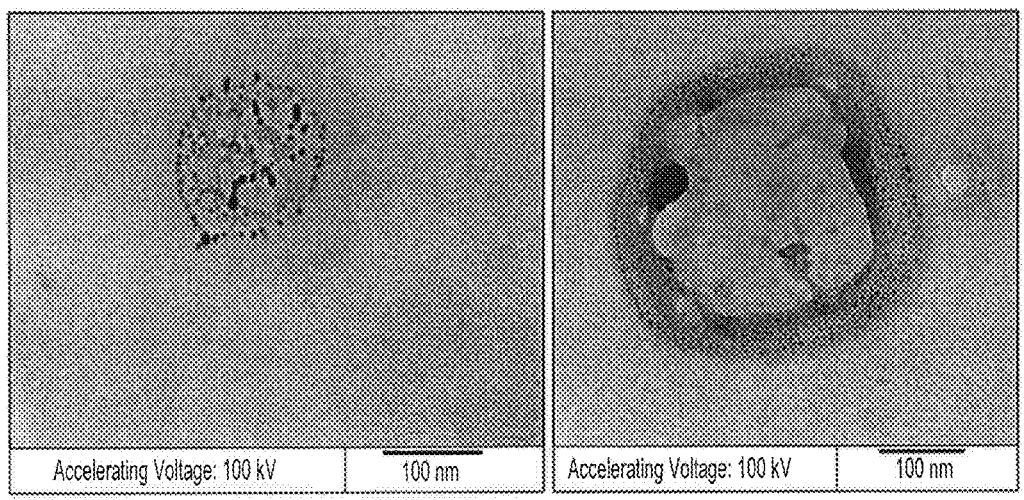
FIG. 2A depicts a transmission electron micrograph of black eggplant skin nanoparticles at 250,000×.
FIG. 2B depicts a transmission electron micrograph of black eggplant skin nanoparticles at 250,000×.

As shown in the transmission electron micrographs of FIGS. 2A-2B, the black eggplant skin nanoparticles are surrounded by a thin layer of organic material. The black eggplant skin nanoparticles are spherical in shape (FIGS. 2A-2B).

Example 2

Antioxidant Activity of Black Eggplant Skin Nanoparticles and Black Eggplant Skin Extracts The antioxidant activities of black eggplant skin nanoparticles and black eggplant skin extracts prepared according to Example 1 were measured as follows.

Total content of phenolic compounds was determined by the Folin-Ciocalteu method. A volume of about 2.5 ml of distilled water and about 0.1 ml of a black eggplant skin sample (nanoparticles or extract) were added to a test tube, followed by addition of about 0.1 ml of undiluted commercially available Folin-Ciocalteu reagent (Sigma-Aldrich, St. Louis, Mo., USA). The solution was mixed well and allowed to stand for about 6 min before about 0.5 ml of a 20% sodium carbonate solution was added. Color developed over about 30 min at room temperature (about 20° C.), and absorbance was measured at 760 nm using a spectrophotometer (Milton Roy Spectronic 1201, USA). A blank was prepared using 0.1 ml of methanol instead of the sample extract. The measurement was compared to a calibration curve of gallic acid solutions and expressed as mg gallic acid equivalents per gram of dry weight sample. (See Table 1).

The total flavonoid content was determined by the aluminum chloride colorimetric method. In brief, about 50 µL of a sample (nanoparticles or extract) was first mixed with about 4 mL of distilled water and then with about 0.3 mL of 5% $NaNO_2$ solution. After about 5 min of incubation, about 0.3 mL of 10% $AlCl_3$ solution was added and the resulting mixture was allowed to stand for about 6 minutes. About 2 ml of 1 mol/L NaOH solution was added and the final volume of the mixture was raised to about 10 ml with distilled water. The mixture was allowed to stand for about 15 min, and absorbance was measured at 510 nm. The total flavonoid content was calculated from a calibration curve, and the result was expressed as mg rutin equivalent per g dry weight or mg catechin equivalent per g dry weight. (See Table 1).

The ability of the samples (nanoparticles/extract) to scavenge DPPH radicals was determined according to the method of Karakaya and Akillioglu. An about 0.08 mM DPPH radical solution in methanol was prepared, and about 950 µL of the DPPH solution was added to about 50 µL of each sample and incubated for 5 min. Exactly 5 min later absorbance readings of the mixture were recorded at 515 nm (Cary 50 Scane; Varian). Both the samples and the DPPH control were measured against a blank Methanol. Antioxidant Activity (AA) was expressed as percentage inhibition of DPPH radical by using the equation AA=100-[100× $(A_{sample}/A_{control})$] where $A_{sample}$ is the absorbance of the sample at t=5 min, and $A_{control}$ is the absorbance of the control DPPH solution. (See Table 1).

The ABTS$^+$ assay was used according to the method of Gouveia and Castilho. The ABTS$^+$ radical solution was prepared by reacting about 50 ml of 2 mM ABTS solution with about 200 µL of 70 mM potassium persulfate solution. This mixture was stored in the dark for 16 h at room temperature, and it was stable in this form for two days. For each analysis, the ABTS$^+$ solution was diluted with pH 7.4 phosphate buffered saline (PBS) solution to an initial absorbance of 0.700±0.021 at 734 nm. This solution was newly prepared for each set of analysis performed. To determine antiradical scavenging activity, an aliquot of about 100 µL methanolic solution was added to 1.8 mL of ABTS$^+$ solution and the absorbance decrease, at 734 nm, was recorded over 6 min. Results were expressed as µmol Trolox equivalent per g of dried sample (g Trolox/g), based on the Trolox calibration curve. (See Table 1).

Ferric reducing antioxidant power (FRAP) was determined according to the procedure described by Benzie and Strain. The FRAP reagent included 300 mM acetate buffer, pH 3.6, 10 mM TPTZ in 40 mM HCl and 20 mM FeCl$_3$ in the ratio 10:1:1 (v/v/v). Three ml of the FRAP reagent was mixed with 100 µL of the sample (nanoparticles/extract) in a test tube and vortexed in the incubator at 37° C. for 30 min in a water bath. After 4 min, reduction of ferric-tripyridyl-triazine to the ferrous complex formed an intense blue color which was measured using a UV-vis spectrophotometer (Cary 50; Varian) at 593 nm. Results were expressed in terms of mmol Trolox equivalent per g of dried sample (g Trolox/g). (See Table 1).

TABLE 1

Determination of Antioxidant Activity of Black Eggplant Skin Extract/Nanoparticles

| Black Eggplant Skin | T. Phenols (mg Gallic acid/ g sample) | T. Flavonoids (mg Catachin/ g sample) | T. Flavonoids (mg Rutin/ g sample) |
|---|---|---|---|
| Extract | 59.376 ± 0.853 | 1.167 ± 0.032 | 11.121 ± 0.349 |
| Nanoparticles | 156.935 ± 4.944 | 2.705 ± 0.133 | 26.356 ± 1.469 |

| Black Eggplant Skin | DPPH (%) | ABTS (g Trolox/ g sample) | FRAP (g Trolox/ g sample) |
|---|---|---|---|
| Extract | 87.62 ± 0.250 | 5.728 ± 0.054 | 1.578 ± 0.012 |
| Nanoparticles | 96.692 ± 0.412 | 5.493 ± 0.136 | 3.739 ± 0.214 |

As illustrated in Table 1, many more total phenols were found in eggplant skin nanoparticles than in the eggplant skin extract. Further, total flavonoids, DPPH radical scavenging, and FRAP were all increased in the nanoparticles when compared to the extracts. These data demonstrate the increased antioxidant capacity of the eggplant skin nanoparticles.

Example 2

Antimicrobial Activity of Black Eggplant Skin Nanoparticles and Black Eggplant Skin Extracts The agar diffusion method was used to determine the antimicrobial activity of black eggplant skin nanoparticles and black eggplant skin extracts synthesized according to the method of Example 1 against a variety of microbes. In brief, bacterial strains were grown on Brain Heart Infusion agar (Oxoid CM 1136) for about 24 hours at 37° C. and about 100 µl of 10$^6$ CFU/ml of each active bacterial strain were spread on the surface of Muller Hinton agar plates (Oxoid CM 0337). About 50 µg/ml of black eggplant skin nanoparticles were dissolved in methanol and left overnight in the refrigerator. Three holes were bored in each agar plate using a sterile cork borer with a diameter of 6 mm, and a volume (about 100 µL) of the dissolved black eggplant skin nanoparticles and the black eggplant skin extracts were introduced into individual wells, (hole "C" contained 100 µl methanol as a control, hole "EN" contained the black eggplant nanoparticles, and hole "N" contained the black eggplant skin extract). The agar plates were incubated at about 37° C. for about 24 hours. The resulting zone of inhibition was measured for every strain, as illustrated in FIGS. 3A-3O.

As shown in FIGS. 3A-3O, the growth of all tested bacterial strains was affected more by the black eggplant skin nanoparticles than by the black eggplant skin extract. Generally black eggplant skin nanoparticles were equally effective in inhibiting the growth of gram positive bacteria and gram negative bacteria, and had inhibitory effects on some yeasts.

It is to be understood that the synthesis of black eggplant (*Solanum melongena*) skin antioxidant nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing black eggplant skin nanoparticles, comprising:
    (a) extracting black eggplant skins in a solvent to produce a black eggplant skin extract;
    (b) spraying the black eggplant skin extract into boiling water under ultrasonic conditions to form a sonicated mixture;
    (c) stirring the sonicated mixture to provide a stirred mixture; and
    (d) drying the stirred mixture to obtain black eggplant skin nanoparticles.

2. The method of synthesizing black eggplant skin nanoparticles according to claim 1, wherein the black eggplant skins are *Solanum melongena* skins.

3. The method of synthesizing black eggplant skin nanoparticles according to claim 2, wherein the *Solanum melongena* skins are skins of *Solanum melongena* collected in Riyadh, Saudi Arabia.

4. The method of synthesizing black eggplant skin nanoparticles according to claim 1, wherein the solvent is methanol.

5. The method of synthesizing black eggplant skin nanoparticles according to claim 1, wherein about 500 mg of black eggplant skins are extracted in about 20 ml of solvent.

6. The method of synthesizing black eggplant skin nanoparticles according to claim 1, wherein the black eggplant skin extract is sprayed into about 40 ml of the boiling water.

7. The method of synthesizing black eggplant skin nanoparticles according to claim 1, wherein the black eggplant skin extract is sprayed into the boiling water dropwise, at a flow rate of about 0.2 ml per minute, for about 5 minutes.

8. The method of synthesizing black eggplant skin nanoparticles according to claim 1, wherein the ultrasonic conditions include an ultrasonic power of 750 W and a frequency of 20 kHz.

9. The method of synthesizing black eggplant skin nanoparticles according to claim 8, wherein the mixture is sonicated for about 10 minutes.

10. The method of synthesizing black eggplant skin nanoparticles according to claim 9, wherein the sonicated mixture is stirred at 200-800 rpm at room temperature for about 20 minutes.

\* \* \* \* \*